US00PP16302P2

(12) United States Plant Patent
Strope

(10) Patent No.: US PP16,302 P2
(45) Date of Patent: Feb. 28, 2006

(54) **NEW GUINEA *IMPATIENS* PLANT NAMED 'BALCEBIMPU'**

(50) Latin Name: *Impatiens hawkeri*
Varietal Denomination: Balcebimpu

(75) Inventor: Kerry M. Strope, Jefferson City, MO (US)

(73) Assignee: Ball Horticultural Company, West Chicago, IL (US)

( * ) Notice: Subject to any disclaimer, the term of this patent is extended or adjusted under 35 U.S.C. 154(b) by 47 days.

(21) Appl. No.: 11/011,336

(22) Filed: Dec. 13, 2004

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
(74) *Attorney, Agent, or Firm*—Wood, Phillips, Katz, Clark & Mortimer

(57) ABSTRACT

A new and distinct New Guinea *Impatiens* plant named 'Balcebimpu' characterized by its large, single purple-colored flowers, dark green-colored glossy foliage, good basal branching, and upright and mounded growth habit.

1 Drawing Sheet

Latin name of genus and species of plant claimed: *Impatiens hawkeri.*

Variety denomination: 'Balcebimpu'.

BACKGROUND OF THE INVENTION

The present invention relates to a new and distinct cultivar of New Guinea *Impatiens* plant botanically known as *Impatiens hawkeri* and hereinafter referred to by the cultivar name 'Balcebimpu'.

The new cultivar originated in a controlled breeding program during May 2001 at Arroyo Grande, Calif. The objective of the breeding program was the development of new *Impatiens* cultivars with numerous, single flowers, excellent basal branching, and compact, mounded growth habit.

The female (seed) parent of the new cultivar was the proprietary *Impatiens hawkeri* selection designated 2835-1, not patented, characterized by its open, loose habit and dull foliage appearance. The male (pollen) parent of the new cultivar was the proprietary *Impatiens hawkeri* selection designated 2601-1, not patented, characterized by its dark purple-colored flowers and medium green-colored foliage. The new cultivar was discovered and selected by the inventor as a single flowering plant within the progeny of the stated cross-pollination during October 2001 at Arroyo Grande, Calif.

Asexual reproductiom of the new cultivar by terminal stem cuttings since October 2001 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balcebimpu' as a new and distinct cultivar of New Guinea *Impatiens* plant:

1. Large, single, bright purple-colored flowers.
2. Dark green-colored glossy foliage.

3. Good basal branching character.
4. Upright and mounded growth habit.

Plants of the new cultivar differ from plants of the female parent primarily in plant habit and foliage appearance and from the male parent primarily in flower color and foliage color.

Of the many commercially available New Guinea *Impatiens* cultivars known to the inventor, the most similar to the new cultivar is the variety 'Balcebpurp', U.S. Plant Pat. No. 13,999. However, in side-by-side comparisons conducted at West Chicago, Ill., plants of the new cultivar differ from plants of 'Balcebpurp' in the following characteristics:

1. Plants of the new cultivar have smaller leaves than plants of 'Balcebpurp'.
2. The flowers of the new cultivar are more blue in color than the flowers of 'Balcebpurp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balcebimpu'. The plants were grown in 10 cm pots for 9 weeks in a greenhouse at West Chicago, Ill.

DETAILED BOTANICAL DESCRIPTION

Figure 1:
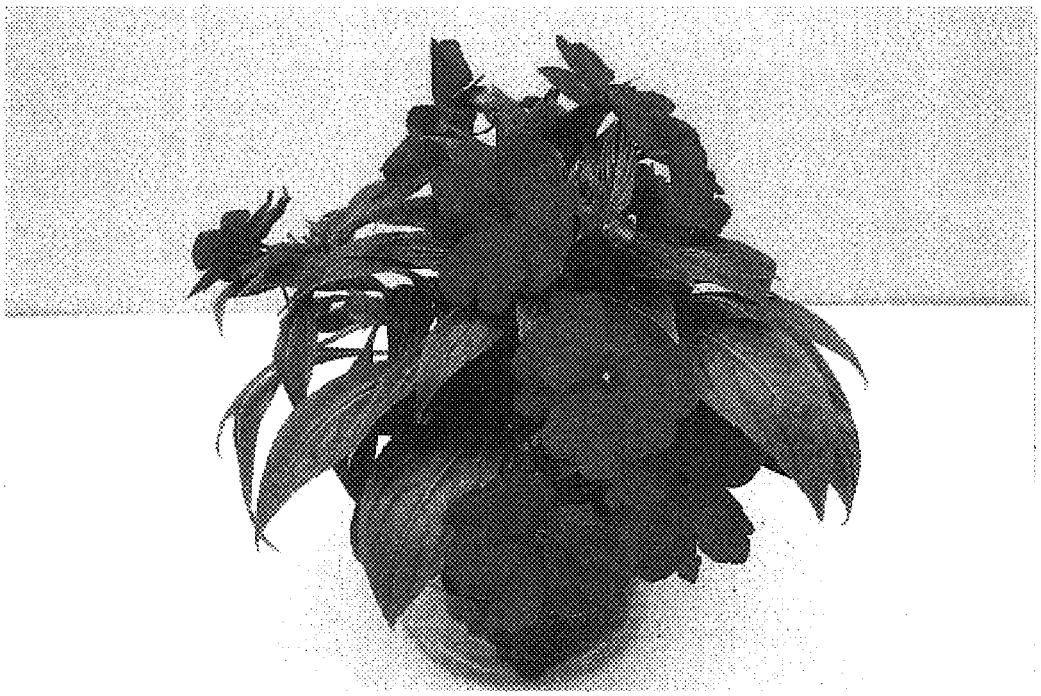
FIG. 1 illustrates a side view of the overall growth and flowering habit of 'Balcebimpu'.
Figure 2:
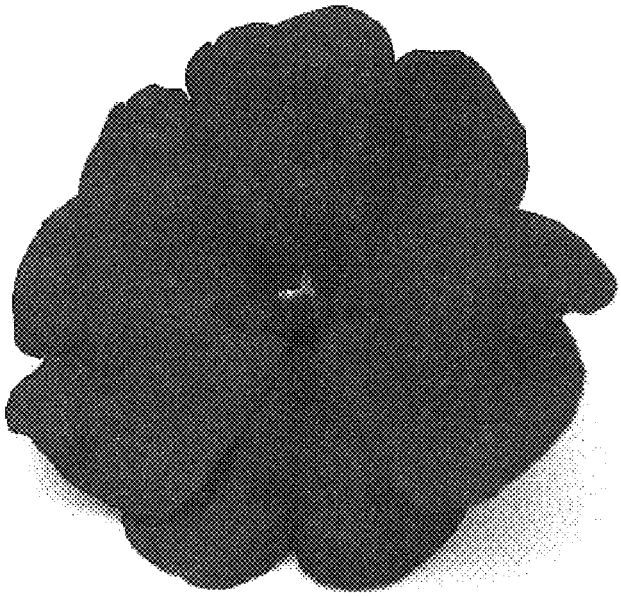
FIG. 2 illustrates a close-up view of an individual flower of 'Balcebimpu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 24, 2004 between 10:00 and 11:45 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 weeks using a soil-less growth medium. Greenhouse temperatures were maintained at approximately 65°–75° F. during the day and approximately 55°–62° F. during the night. Greenhouse light levels were maintained at approximately 4,000–6,000 footcandles during the day.

Botanical classification: *Impatiens hawkeri* cultivar Balcebimpu.

Parentage:

*Female (seed) parent.*—Proprietary *Impatiens hawkeri* selection designated 2835-1, not patented.

*Male (pollen) parent.*—Proprietary *Impatiens hawkeri* selection designated 2601-1, not patented.

Propagation:

*Type cutting.*—Terminal stem.

*Time to initiate roots.*—Approximately 7–14 days with the shorter times generally being experienced in the summer and the longer times in the winter.

*Time to produce a rooted cutting.*—Approximately 21 days.

*Root description.*—Fine, fibrous.

*Rooting habit.*—Freely branching.

Plant description:

*Crop time.*—Approximately 6–8 weeks from a rooted cutting to finish.

*Growth habit.*—Compact with good basal branching.

*Form.*—Upright and mounded.

*Size.*—Height to top of plant plane: Approximately 14.8 cm. Width (plant spread): Approximately 27.6 cm.

*Branch.*—Quantity: Approximately 3 per plant. Strength: Strong. Length: Approximately 12 cm. Diameter: Approximately 9.8 mm. Texture: Pubescent. Color: 144B with 185A at nodes. Internode length: Approximately 2.3 cm.

*Foliage.*—Quantity per branch: Approximately 19. Fragrance: None. Type: Simple. Arrangement: Whorls of 5. Aspect: At right angle to stem. Shape: Lanceolate. Apex: Acuminate. Base: Attenuate. Margin: Serrulate/ciliate. Venation pattern: Pinnate, arcuate. Length of mature foliage: Approximately 8.5 cm. Width of mature foliage: Approximately 3.2 cm. Texture of upper surface: Short stiff hairs. Texture of lower surface: Glabrous except for short stiff hairs along mid-vein. Color of upper surface of mature foliage: 139A, with veins and mid-vein of 145C. Color of lower surface of mature foliage: Closest to 138B with veins and mid-vein of 145C. Petiole length: Approximately 5 cm. Petiole diameter: Approximately 2.6 mm. Petiole texture: Both surfaces are glabrous. Petiole color: Upper surface: 145C with streaks of 185A. Lower surface: 145C.

Flowering description:

*Flowering habit.*—Freely flowering under outdoor growing conditions with substantially continuous blooming from spring through autumn and year round in greenhouse environment.

*Time to first flower.*—Approximately 8 weeks from a rooted cutting.

*Lastingness of individual bloom.*—Approximately 5–7 days.

*Quantity of flowers per plant.*—Approximately 10 flowers and 12 buds at any one time.

Flower description:

*Flower bud rate of opening.*—Generally it takes from 7 to 10 days for buds to progress from first color to fully open flowers.

*Mature flower buds (just before opening).*—Shape: Elliptic. Length: Approximately 1.7 cm. Diameter: Approximately 9.8 mm. Color: Between N74A and N78A.

*Flower description.*—Type: Single. Fragrance: None. Shape: Round. Diameter: Approximately 6.5 cm. Depth: Approximately 1.4 cm. Borne: Above foliage facing upward or outward. Flowers are not persistent or fragrant.

*Petals.*—Quantity per flower: 5. Shape: Obovate. Margin: Entire. Apex: Emarginate. Base of upper petal: Truncate. Base of lateral and lower petals: Attenuate. Texture: Glabrous. Appearance: Iridescent. Size of upper petal: Length: Approximately 2.9 cm. Width: 4.8 cm. Size of lateral petals: Length: 3.5 cm. Width: 3.5 cm. Size of lower petals: Length: 3.6 cm. Width: 3.8 cm.

*Flower color.*—Upper surface of petals when fully open: Darker than N74A. Lower surface of petals when fully open: Closest to N74A.

*Calyx.*—Quantity of sepals: Three. Sepal texture: Both surfaces are glabrous. Lateral sepal shape: Ovate. Lateral sepal apex: Acuminate. Lateral sepal length: Approximately 1.3 cm. Lateral sepal width: Approximately 6.7 mm. Lateral sepal color: Both surfaces are 144D with 144B at apex and venation of 144B and spots of 185A. Lower sepal shape: Ovate. Lower sepal apex: Acuminate. Lower sepal base: Forms spur. Lower sepal length: Approximately 1.7 cm. Lower sepal width: Approximately 1.3 cm. Lower sepal color: Upper surface gradually transitions from 70A to 70B with 145C at tip. Lower surface is 70C.

*Spur.*—Quantity: One per flower. Length: Approximately 5.0 cm. Diameter at base: Approximately 2.5 mm. Diameter at tip: Approximately 0.9 mm. Texture: Glabrous. Color: 187B with tip of 144A.

*Peduncle.*—Length: Approximately 4.2 cm. Diameter: Approximately 2.0 mm. Texture: Glabrous. Strength: Strong. Angle to stem: Acute. Color: 144B with overlay of 183B.

*Reproductive organs.*—Stamen number: 5. Anther shape: Hooded. Anther length: 4 mm. Anther color: 9C. Pollen amount: Abundant. Pollen color: 11C. Pistil quantity: 1. Stigma shape: Five pointed star. Stigma length: 1.0 mm. Stigma color: Transparent. Style length: 8.0 mm. Style color: Translucent. Ovary length: 6.6 mm. Ovary diameter: 2.5 mm. Ovary texture: Glabrous. Ovary color: 143A.

Seed and fruit development: Neither seed nor fruit production has been observed.

Disease and pest resistance: Resistance to pathogens and pests common to New Guinea *Impatiens* has not been observed.

What is claimed is:

1. A new and distinct cultivar of New Guinea *Impatiens* plant named 'Balcebimpu', substantially as herein shown and described.

* * * * *